(12) United States Patent
Nishida et al.

(10) Patent No.: US 7,557,224 B2
(45) Date of Patent: Jul. 7, 2009

(54) METHOD FOR RECOVERING LACTIDE FROM POLYLACTIC ACID OR DERIVATIVE THEREOF

(75) Inventors: Haruo Nishida, Fukuoka (JP); Yujiang Fan, Ibaraki (JP); Yoshihito Shirai, Fukuoka (JP)

(73) Assignees: Kyushu Institute of Technology, Fukuoka (JP); Kitakyushu Foundation for the Advancement of Industry, Science and Technology, Fukuoka (JP)

( * ) Notice: Subject to any disclaimer, the term of this patent is extended or adjusted under 35 U.S.C. 154(b) by 98 days.

(21) Appl. No.: 11/579,144

(22) PCT Filed: Apr. 25, 2005

(86) PCT No.: PCT/JP2005/007813

§ 371 (c)(1),
(2), (4) Date: Oct. 30, 2006

(87) PCT Pub. No.: WO2005/105775

PCT Pub. Date: Nov. 10, 2005

(65) Prior Publication Data

US 2008/0004454 A1    Jan. 3, 2008

(30) Foreign Application Priority Data

Apr. 30, 2004    (JP) .............................. 2004-135476

(51) Int. Cl.
    *C07D 323/04*    (2006.01)
(52) U.S. Cl. ..................................................... 549/274
(58) Field of Classification Search ................... 549/274
    See application file for complete search history.

(56) References Cited

U.S. PATENT DOCUMENTS

2003/0187181 A1*  10/2003  Sakane et al. ............... 528/355

FOREIGN PATENT DOCUMENTS

| DE | 43 25 849 A1 | 2/1995 |
|---|---|---|
| JP | 6-279434 A | 10/1994 |
| JP | 9-3184 A | 1/1997 |
| JP | 10-168077 A | 6/1998 |
| JP | 10-306091 A | 11/1998 |
| JP | 2000-15107 A | 1/2000 |
| JP | 2001-303387 A | 10/2001 |
| JP | 2003-192925 A | 7/2003 |
| JP | 2003-192929 A | 7/2003 |
| JP | 2004-75772 A | 3/2004 |

OTHER PUBLICATIONS

Philippe Degee et al., Bulk polymerization of lactides initiated by aluminium isopropoxide, 3$^{a)}$, Macromolecular Chemistry and Physics, vol. 198, pp. 1985-1998, (1997).
Masaki Noda et al., "LL-Lactide Formation from Thermal Depolymerization Reaction of Poly (L-lactic acid) Oligomer (II)", vol. 56, No. 3-4, pp. 169-173, (Feb. 2000).
Masaki Noda et al., Thermal Catalytic Depolymerization of Poly(L-Lactic Acid) Oligomer into LL-Lactide: Effects of Al, Ti, Zn and Ar Compounds as Catalysts, Chemical & Pharmaceutical Bulletin, vol. 47(4), pp. 467-471 (Apr. 1999).
Ayaki Miyayu, "Poly Nyusan o Shuseibun to suru Plastic Seihin no Chemical Recycle nit suite", The Society of Chemical Engineers, Japan Nenkai Kenkyuu Happyo Koen Yoshishu, vol. 69$^{th}$, p. 234, (Mar. 2, 2004).
Yoshito Shiroi, "Poly Nyusan no Chemical Recycle to Junkan Shakai System", Kogyo Zairyo, vol. 51, No. 3, pp. 27-29, (2003).
D. Carn et al., Influence of residual monomers and metals on poly (L-lactide) thermal stability, Polymer, vol. 38, No. 8, pp. 1879-1884, (1997).
Yujiang Fan et al., "Effect of Aluminum Compounds on Thermal Degradation of Poly Lactic Acid", Polymer Preprints, Japan, (CD-ROM), vol. 53, No. 1, pp. 2204 (IK10), (May 10, 2004).
Haruo Nishida et al, "Chemical Recycling of Flame Resistant Poly(L-lactic acid)/Aluminum Hydroxide Composites", Polymer Preprints, Japan (CD-ROM), vol. 53, No. 2, pp. 5591-5592 (3X03), (Sep. 1, 2004).
Haruo Nishida et al, "Chemical Recycling of Flame Resisting Poly(L-lactic acid) Composites", Polymer Zairyo Forum Koen Yokoshu, vol. 13$^{th}$, p. 145, (Oct. 28, 2004).

* cited by examiner

*Primary Examiner*—Janet L Andres
*Assistant Examiner*—David E Gallis
(74) *Attorney, Agent, or Firm*—Sughrue Mion, PLLC

(57) ABSTRACT

To provide an efficient method for recovering and producing lactide having high optical purity by depolymerizing a polylactic acid or derivative thereof in order to carry out chemical recycling of the polylactic acid or derivative thereof or of a resin composition comprising same, wherein a mixture of a polylactic acid or derivative thereof and aluminum hydroxide is thermally decomposed at a temperature in a range from at least the melting temperature of the polylactic acid or derivative thereof to no greater than 320° C., thus recovering lactide.

17 Claims, 2 Drawing Sheets

METHOD FOR RECOVERING LACTIDE FROM POLYLACTIC ACID OR DERIVATIVE THEREOF

TECHNICAL FIELD

Figure 1:
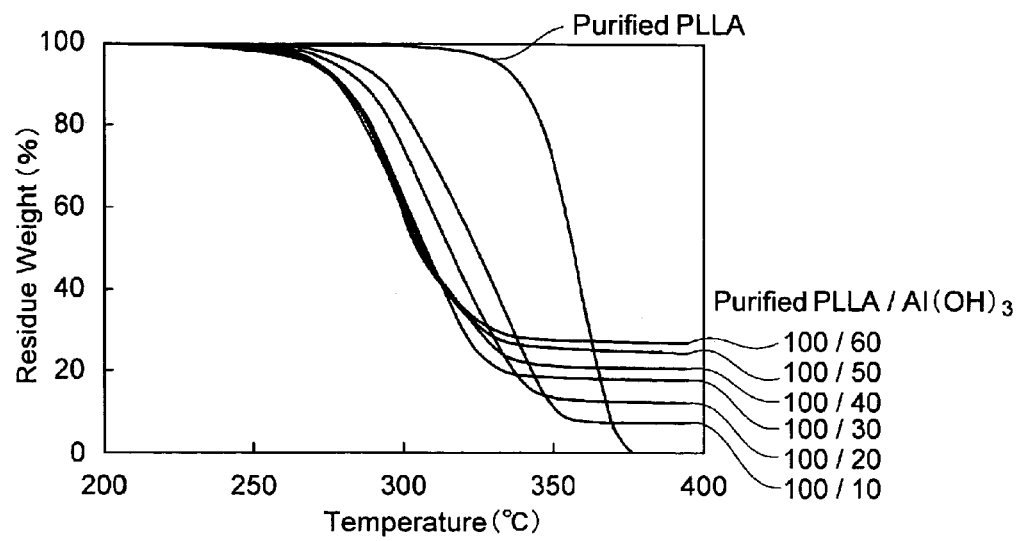

The present invention relates to a method for recovering lactide from a polylactic acid or derivative thereof and, more particularly, to a chemical recycling method for recovering and producing lactide, which is a cyclic dimer of lactic acid, by depolymerizing a polylactic acid or derivative thereof, either from the polylactic acid or derivative thereof on its own, or from a resin composition comprising same.

BACKGROUND ART

In recent years, awareness of environmental problems has been rising, and it has been pointed out that there is a possibility that halogen compounds, which have been widely used as flame retardants for plastic materials used in electrical or electronic apparatus products, might generate dioxins when the materials are incinerated for disposal. Because of this, there has been a shift to non-halogen flame retardants. Among these, as safe inorganic flame retardants having a large endothermic heat of decomposition, there is high demand for metal hydroxides, and aluminum hydroxide in particular, and the use thereof is further encouraged by the decomposition product being alumina, which is chemically stable. However, in recent years, there has been increasing concern about flame retarding materials inhibiting combustion when they are disposed of.

In order to solve the problem of global warming due to an increase in carbon dioxide, instead of plastic materials synthesized from fossil fuels, the utilization of a lactic acid polymer, which is synthesized from a renewable resource biomass and can be biorecycled and chemically recycled, is being actively developed. The advantage of using a lactic acid polymer is that, since the lactic acid polymer is synthesized from a biomass formed by fixing carbon dioxide, even if it is incinerated there is very little increase in carbon dioxide in the process overall, which supports the concept of carbon neutrality. Chemical recycling is a method in which an original starting material is regenerated using a small amount of energy, and is a method that is a step beyond the concept of carbon neutrality as an environmental countermeasure.

As a method for producing a lactic acid polymer, a technique of producing a lactic acid polymer by synthesizing lactide from a lactic acid oligomer by thermal decomposition and further polymerizing the lactide is well known in the art. In this production process, it is important to maintain optical purity. This is because a lactic acid polymer suitable for practical use is a transparent high rigidity polymer that is produced by ring-opening polymerization of an optically active L,L-lactide and has a melting point of about 175° C., and even a small decrease in the optical activity causes a large decrease in the melting point, resulting in loss of its utility.

A method in which, in order to impart flame retardancy to a lactic acid polymer synthesized from a renewable resource, a safe metal hydroxide such as aluminum hydroxide is used as a flame retardant, is already known from, for example, the publications below (ref. Patent Publications 1 to 3). However, the purpose of making the lactic acid polymer flame retardant is to suppress combustion or thermal decomposition thereof at high temperature, and a method in which the starting material lactide is recovered by thermal decomposition of a lactic acid polymer in the flame retardant composition is not disclosed in any of the publications.

Apart from making the lactic acid polymer flame retardant, the use of a metal compound as a catalyst when recovering the starting material lactide by thermal decomposition of the lactic acid polymer is also known. For example, with regard to thermal decomposition of a lactic acid polymer by an aluminum compound, Degee et al. have polymerized lactide using aluminum isopropoxide as an initiator and have further carried out thermal decomposition of the lactic acid polymer so produced (ref. Non-Patent Publication 1). Furthermore, Noda and Okuyama have carried out thermal decomposition of a lactic acid oligomer using aluminum isopropoxide and aluminum ethylacetoacetate, and have measured the purity of the lactide obtained as a decomposition product (ref. Non-Patent Publication 2). However, these techniques, which employ an aluminum compound, only disclose that the lactide thus recovered has very low optical purity.

Moreover, among patent publications, JP-A-6-279434 (Patent Publication 4) (JP-A denotes a Japanese unexamined patent application publication) discloses a technique for obtaining lactide having low optical purity (meso-isomer content 7-40%) from a lactic acid oligomer by the combined use of an alkali metal salt and a metal of group 4 to 15 in the periodic table and/or a salt thereof. The amount of a thermal decomposition catalyst added in this case is in the range of 0.01-5 parts by weight. JP-A-10-168077 (Patent Publication 5) and JP-A-10-306091 (Patent Publication 6) disclose, as thermal decomposition catalysts for a lactic acid oilgomer, metal compounds formed from group IIIA, group IVA, group IIB, group IVB, and group VA, and disclose, as aluminum compounds, aluminum ethoxide, aluminum isopropoxide, aluminum oxide, and aluminum chloride, which are compounds that do not function as flame retardants. JP-A-2000-15107 (Patent Publication 7) discloses a technique in which a special cyclic alkoxyaluminum compound is used as a thermal decomposition catalyst for a lactic acid oligomer at 0.1-1 mol % of the entire lactic acid units. None of these publications disclose a specific lactide recovery technique employing a metal hydroxide such as aluminum hydroxide.

As hereinbefore described, there is no technical disclosure in the art of a composition comprising a lactic acid polymer and a metal hydroxide such as aluminum hydroxide as a flame retardant, wherein recovery of lactide having high optical purity from the lactic acid polymer in the composition and the flame retardant are associated. This is because the concept of flame retardance, which is to suppress decomposition and combustion, and the concept of chemical recycling, which is to control the promotion of decomposition, are mutually contradictory. In addition, it has been shown in the art that, for example, recovery of lactide using an aluminum compound tends to degrade the optical purity. Under such circumstances, there has been a desire for a new technology that can achieve a balance between flame retardance and efficient recovery of lactide having high optical purity in order to apply a lactic acid polymer produced from a renewable resource to, for example, electrical and electronic apparatus components and carry out chemical recycling thereof economically.

(Patent Publication 1) JP-A-2001-303387
(Patent Publication 2) JP-A-2003-192925
(Patent Publication 3) JP-A-2004-75772
(Patent Publication 4) JP-A-6-279434
(Patent Publication 5) JP-A-10-168077
(Patent Publication 6) JP-A-10-306091
(Patent Publication 7) JP-A-2000-15107
(Non-Patent Publication 1) P. Degee et al., 'Macromolecular Chemistry and Physics, Vol. 198, 1985 (1997)'

(Non-Patent Publication 2) Noda and Okuyama, 'Shimadzu Hyouron (Shimadzu Review), Vol. 56, 169 (2000); M. Noda and H. Okuyama, Chemical & Pharmaceutical Bulletin, Vol. 47, 467 (1999)'

DISCLOSURE OF INVENTION

Problems to be Solved by the Invention

It is an object of the present invention to provide an efficient method for recovering and producing lactide having high optical purity by depolymerizing a polylactic acid or derivative thereof in order to carry out chemical recycling of the polylactic acid or derivative thereof or of a resin composition comprising same.

Means for Solving the Problems

The object of the present invention can be attained by a method in which lactide is recovered by thermally decomposing a mixture of a polylactic acid or derivative thereof and aluminum hydroxide at a temperature in the range from at least the melting temperature of the polylactic acid or derivative thereof to no greater than 320° C.

BRIEF DESCRIPTION OF DRAWINGS (FIG. 1) TG/DTA curve of a purified poly(L-lactic acid)/aluminum hydroxide composition (FIG. 2) TG/DTA curve of a tin-containing poly(L-lactic acid)/aluminum hydroxide composition (FIG. 3) TG/DTA curve of a tin-containing poly(L-lactic acid)/polystyrene/aluminum hydroxide composition

BEST MODE FOR CARRYING OUT THE INVENTION

The present invention is a method for recovering lactide by thermally decomposing a mixture of a polylactic acid or derivative thereof and aluminum hydroxide at a temperature in the range from at least the melting temperature of the polylactic acid or derivative thereof to no greater than 320° C., and preferably 200° C. to 300° C. As described above in the Background Art section of the present invention, a composition of a polylactic acid or derivative thereof and aluminum hydroxide itself is known as a flame retardant composition. However, as described in detail in Examples, which will be described later, the actual temperature range to which the lactic acid polymer composition is exposed during combustion (about 650° C. or higher for a burning cigarette and 1200° C. or higher for a flame) is very different from the controlled temperature range during chemical recycling, and the type of reaction proceeding in each temperature range is also different. Although it is known that aluminum hydroxide functions as a flame retardant during combustion, it has been found for the first time by the present invention that aluminum hydroxide functions effectively as a decomposition catalyst for the chemical recycling and, moreover, lactide having very high optical purity can be recovered in the temperature range of the present invention.

In the present invention, the mixture of a polylactic acid or derivative thereof and aluminum hydroxide is thermally decomposed at a temperature in the range from at least the melting temperature of the polylactic acid or derivative thereof to no greater than 320° C., and preferably 200° C. to 300° C., and lactide having high optical purity is selectively recovered. Hardly any thermal decomposition of a polylactic acid or derivative thereof takes place at a temperature that is equal to or less than the melting temperature of the polylactic acid or derivative thereof; when the temperature exceeds 320° C., racemization of the lactic acid ester structural unit in the polylactic acid or derivative thereof proceeds readily, as a result formation of meso-lactide is promoted, and the optical purity of the lactide thus obtained is degraded. A preferred temperature range is 200° C. to 300° C., and a more preferred temperature range is 250° C. to 300° C. This temperature range depends on the molecular weight of the polylactic acid or derivative thereof. In general, the lower the molecular weight of a polymer, the lower the temperature range in which decomposition proceeds. However, racemization of the lactic acid ester structural unit becomes noticeable at a temperature exceeding 320° C. regardless of the molecular weight. Such knowledge concerning the decomposition function of aluminum hydroxide and the temperature-dependent decomposition characteristics has been found for the first time in the present invention.

The polylactic acid or derivative thereof referred to in the present invention is a polymer having a lactic acid ester structure as a principle unit and, in particular, a polymer having an L- or D-lactic acid ester structural unit at 90% or greater of the entire units, preferably 95% or greater, and more preferably 98% or greater. As a component other than the L- or D-lactic acid ester structural unit, a copolymer component unit derived from a lactone, a cyclic ether, a cyclic amide, a cyclic acid anhydride, etc., which are copolymerizable with lactide, may be present. Examples of copolymer components that can be suitably used include lactones such as caprolactone, valerolactone, β-butyrolactone, and p-dioxanone; cyclic ethers such as ethylene oxide, propylene oxide, butylene oxide, styrene oxide, phenylglycidyl ether, oxetane, and tetrahydrofuran; cyclic amides such as ε-caprolactam; and cyclic acid anhydrides such as succinic anhydride and adipic anhydride. Furthermore, it is possible to use an alcohol, a glycol, a glycerol, another polyhydric alcohol, a carboxylic acid, a polybasic carboxylic acid, a phenol, etc. as a unit that can be present in the polylactic acid or derivative thereof as an initiator component. Specific examples of the initiator component suitably used include ethylhexyl alcohol, ethylene glycol, propylene glycol, butanediol, polyethylene glycol, polypropylene glycol, polyvinyl alcohol, glycerol, octylic acid, lactic acid, and glycolic acid.

The aluminum hydroxide used in the present invention undergoes a dehydration reaction at a temperature of 200° C. or higher, releases 34.6 wt % of water in theory, and changes into alumina. Since there is a large endothermic effect during the dehydration reaction, aluminum hydroxide is used as a flame retardant filler.

It is not at all necessary for the aluminum hydroxide used in the present invention to be a special one. With regard to generally known aluminum hydroxides, there are gibbsite, bayerite, diaspore, boehmite, etc.; gibbsite and bayerite are preferably used, and gibbsite is more preferably used. It is also possible to use two or more types as a mixture, and it is also possible to use a composite compound containing at least 10 wt % of the above-mentioned aluminum hydroxide. Aluminum hydroxide is normally a white powder; the shape is not particularly limited, and one with any shape can be used. When taking into consideration uniform dispersion thereof into the polylactic acid or derivative thereof or the polymer composition comprising same, and the melt-flowability of the mixture, the average particle size thereof is preferably 0.01 to 200 μm, and particularly preferably 1 to 50 μm.

The amount of aluminum hydroxide mixed relative to the polylactic acid or derivative thereof or the polymer composition comprising same is desirably 10 to 100 parts by weight of aluminum hydroxide relative to 100 parts by weight of the polylactic acid or derivative thereof, and preferably 20 to 60 parts by weight. For example, it is convenient for the amount of aluminum hydroxide to be in a range that allows it to function as a flame retardant and also in a range that allows chemical recycling to be carried out, and it is known that as a flame retardant the content thereof in the lactic acid polymer is desirably in the range of 5 to 50 wt % (5.3 to 100 parts by weight relative to 100 parts by weight of polylactic acid). Therefore, when chemical recycling of the present invention is carried out, in a case in which the polylactic acid or derivative thereof does not contain other metals, etc., a polymer containing 5 to 50 wt % of aluminum hydroxide as a flame retardant may be thermally decomposed as it is. However, in order to preferentially carry out the thermal decomposition mechanism by means of aluminum hydroxide while counteracting the influence of other metals, such as for example tin, (used as a polymerization catalyst, etc.) contained in the polylactic acid or derivative thereof, it is necessary to employ at least 10 parts by weight (9.1 wt % as the content in the polymer) of aluminum hydroxide relative to 100 parts by weight of the polylactic acid or derivative thereof. However, it is not preferable for it to exceed 100 parts by weight (50 wt % as the content in the polymer) since the flowability of the polymer is greatly degraded and it becomes difficult to carry out melt-molding.

It is already well known that in the thermal decomposition of a lactic acid polymer the thermal decomposition temperature and the thermal decomposition product depend greatly on the level of trace amounts remaining of a tin compound used as a polymerization initiator (e.g. H. Nishida et al., Polymer Degradation and Stability, Vol. 81, 515 (2003)). When the tin content is 169 ppm or greater, the decomposition temperature of the lactic acid polymer is very low, and lactide having high optical purity is selectively formed as a decomposition product. On the other hand, when the tin content is 60 ppm or less, the decomposition temperature of the lactic acid polymer becomes high, the optical purity of the decomposition product is degraded, and contamination with oligomer becomes noticeable. Such a function of tin is effective in chemical recycling, but since decomposition easily occurs during melt-molding of a lactic acid polymer product, in general as much as possible of the residual tin compound is extracted prior to melt-molding. This is one cause of the high cost of the lactic acid polymer.

According to the investigation by the present inventors, when aluminum hydroxide is added to the lactic acid polymer, interestingly, in a case where the lactic acid polymer contains a large amount of residual tin compound, the thermal decomposition temperature tends to increase in response to an increase in the amount of aluminum hydroxide added (contributing to stability during melt-molding). On the other hand, in the case of a purified lactic acid polymer from which most of the residual tin compound has been extracted, the thermal decomposition temperature tends to decrease in response to an increase in the amount of aluminum hydroxide added. This decrease in the decomposition temperature proceeds according to the amount of aluminum hydroxide added until the amount reaches 30 parts by weight, but beyond 30 parts by weight it converges to a specific temperature region, and no noticeable decrease in the thermal decomposition temperature is observed beyond this. That is, it has been found that the addition of aluminum hydroxide has the effect of making thermal decomposition of the lactic acid polymer converge to a specific temperature range and also an effect in counteracting the outstanding decomposition promotion effect of the tin compound and contributing to stabilization of the lactic acid polymer containing residual tin.

Therefore, in accordance with the knowledge obtained by the present inventors, the polylactic acid or derivative thereof containing a tin compound can easily be melt-molded as a mixture with aluminum hydroxide even without specially removing the tin compound. The present invention can preferably be applied to such a polylactic acid or derivative thereof containing a tin compound.

In the method of the present invention, a mixture of a polylactic acid or derivative thereof and aluminum hydroxide, which is a target of chemical recycling, may be a mixture of a polylactic acid or derivative thereof and aluminum hydroxide alone, or a so-called resin composition comprising, in addition to the above, a resin, a reinforcing fiber, a filler, an additive, etc. Components that can be present are required not to interfere with the flame retarding function of aluminum hydroxide during combustion, and not to interfere with the chemical recycling of the polylactic acid or derivative thereof.

Preferred examples of resins that impart practical physical properties include polyolefins such as polyethylene and polypropylene; styrene resins such as polystyrene, ABS, and AS; polyester resins such as polyethylene terephthalate and polybutylene terephthalate; polycarbonate resins such as polycarbonate (PC), PC/ABS, and PC/AS; vinyl alcohol resins such as polyvinyl alcohol and polyethylene vinyl alcohol; engineering plastics such as modified polyphenylene ether, polyamide, and polyoxymethylene; impact improving rubbers such as butadiene rubber, styrene-butadiene rubber, isoprene rubber, and acrylonitrile-butadiene rubber; and biodegradability improvers such as polyhydroxybutyrate, polyhydroxyalkanoate, polytetramethylene succinate, polytetramethylene succinate adipate, polycaprolactone, polyglycolic acid, polyparadioxanone, acetylcellulose, poly-γ-glutamic acid, and polylysine. The amount of these resins added may be selected as appropriate according to physical properties required for the product, but in general it is 200 parts by weight or less relative to 100 parts by weight of the polylactic acid or derivative-thereof, preferably 100 parts by weight or less, and more preferably 50 parts by weight or less. These resins are normally melted during the chemical recycling of the polylactic acid or derivative thereof, and subjected to material recycling by repelletizing.

The reinforcing fiber and the filler are not particularly limited, and known reinforcing fibers and fillers may be used without any restrictions, but examples of suitably used fibers include glass fiber, carbon fiber, and plant-derived cellulose fiber; examples of suitably used fillers include inorganic fillers such as glass microbeads, chalk, quartz, feldspar, mica, talc, silicate, kaolin, zeolite, alumina, silica, magnesia, ferrite, barium sulfate, and calcium carbonate; and organic fillers such as an epoxy resin, a melamine resin, a urea resin, an acrylic resin, a phenol resin, a polyimide resin, a polyamide resin, an unsaturated polyester resin, and a perfluoro resin, and these fillers may be used singly or in a combination of two or more types. The amount of these fillers added may be selected as appropriate according to physical properties required for the product, and in general it is 200 parts by weight or less relative to 100 parts by weight of the polylactic acid or derivative thereof, preferably 100 parts by weight or less, and more preferably 50 parts by weight or less.

With regard to other additives that can be present in the resin composition comprising the polylactic acid or derivative thereof, there are flame retardants other than aluminum hydroxide, hydrolysis inhibitors, crystallization accelerators, lubricants, UV absorbers, antioxidants, mold release agents, compatibilizing agents, antistatic agents, etc. These additives can be added in a range that does not noticeably affect the flame retardant effect of aluminum hydroxide or chemical recycling of the polylactic acid or derivative thereof, and they are usually used at 5 parts by weight or less relative to 100 parts by weight of the polylactic acid or derivative thereof, and preferably 3 parts by weight or less. Examples of flame retardants other than aluminum hydroxide include boric acid-based flame-retardant compounds; phosphorus-containing flame retardant compounds such as ammonium phosphate and ammonium polyphosphate; inorganic flame retardant compounds such as metal sulfate compounds, antimony-containing compounds, iron oxide compounds, metal nitrate compounds, titanium-containing compounds, zirconium-containing compounds, molybdenum-containing compounds, and aluminum-containing compounds; nitrogen-containing flame retardant compounds such as cyanurate compounds having a triazine ring; silica-based flame retardant compounds such as silicone oil, low melting point glass, and organosiloxane; and colloidal flame retardant compounds such as magnesium hydroxide, calcium hydroxide, and calcium aluminate.

As hydrolysis inhibitors that can be present in the resin composition comprising the polylactic acid or derivative thereof, known hydrolysis inhibitors having the function of inhibiting hydrolysis of the polylactic acid or derivative thereof may be used without any restrictions. Examples of hydrolysis inhibitors that are desirably used include carbodiimide compounds, isocyanate compounds, and oxazoline compounds, and the amount of these hydrolysis inhibitors added is 5 parts by weight or less relative to 100 parts by weight of the polylactic acid or derivative thereof, preferably 3 parts by weight or less, and more preferably 1 part by weight or less.

The resin composition comprising the polylactic acid or derivative thereof can be applied to various uses. For example, the resin composition can be used to obtain a molding such as a casing of an electrical or electronic apparatus such as a radio, a microphone, a television, a keyboard, a portable music reproducing machine, a mobile phone, a personal computer, and various types of recorders. Furthermore, it may be used in applications such as an automobile interior component, various types of packing material, and various types of decorative sheet. Examples of methods for molding these moldings include film molding, sheet molding, extrusion molding, and injection molding, and among them injection molding is preferably employed for molding of electrical or electronic apparatus components. More specifically, extrusion molding may be carried out by a standard method using a known extruder such as, for example, a single shaft extruder, a multiple shaft extruder, or a tandem extruder. Injection molding may be carried out by a standard method using a known injection molding machine such as, for example, an in-line screw injection molding machine, a multilayer injection molding machine, or a dual head injection molding machine.

In the present invention, with regard to a method for mixing the polylactic acid or derivative thereof and aluminum hydroxide, known mixing means may be used without any particular restrictions. The important point in the present invention is that, since it is essential for aluminum hydroxide to be uniformly dispersed in the polylactic acid or derivative thereof, means that allows aluminum hydroxide to be easily and finely dispersed is suitably employed. Examples of adding and mixing methods that are suitably used include a melt mixing method, a solution mixing method, a powder mixing and melt dispersion method, and a master batch method. When the polylactic acid or derivative thereof is a molding on its own or as a resin composition, it may be ground in advance and then mixed with aluminum hydroxide.

In the present invention, as a method for recovering lactide having high optical purity, it is desirable that the polylactic acid or derivative thereof or the polymer composition comprising same is charged into a thermal decomposition reactor whose temperature is set in the range of, for example, 200-320° C., but a method in which the temperature is rapidly increased from a lower temperature can also be selected. As a thermal decomposition reactor that is suitably used, either a batch type or a continuous type can be put into practice. Examples of the reactor desirably used include an extruder, an autoclave, and a fluidized bed reactor. When an extruder is used, it is possible to control the thermal decomposition temperature and the thermal decomposition rate and set the rate of temperature increase in the temperature range of the present invention by setting the temperature of each cylinder block, the rotational speed of a screw, the shape of the screw, and the single shaft/double shaft screw type.

When thermal decomposition of the polylactic acid or derivative thereof is carried out using such a thermal decomposition reactor, the lactide thus formed is volatilized in the gas phase, and it is therefore essential to employ a process that takes out a gas-phase component. The above-mentioned reactors have an outlet through which the gas-phase component is taken out and/or an inlet through which an inert gas such as nitrogen gas is introduced in order to expel and replace the gas-phase component. For example, in the case of an extruder reactor, a vent is suitably used as the outlet. When taking out the gas-phase component through the vent, in general a method in which it is taken out under vacuum is suitably carried out. The degree of vacuum and/or the evacuation speed may be set according to the amount and temperature of vaporized component, and the degree of vacuum is normally 500 mmHg or less, and preferably 200 mmHg or less.

In this way, lactide having high optical purity may be obtained by the chemical recycling in accordance with the method of the present invention. Evaluation of the optical purity of the lactide thus obtained may be carried out by a conventionally known method. For example, when racemization occurs in one lactic acid ester structural unit, and the lactide unit is subsequently released, meso-lactide is formed. When racemization occurs in two adjacent lactic acid ester structural units, and the two lactic acid ester structural units are released as lactide, a lactide that is the opposite optical isomer to the original polylactic acid is formed. In general, when a racemization reaction proceeds randomly, meso-lactide is formed as the main decomposition product. The proportions of the meso-lactide, L,L-lactide, and D,D-lactide may be checked by gas chromatographic analysis. When a column that cannot carry out optical resolution is used, since D,D-lactide and L,L-lactide are detected as the same fraction, evaluation of racemization may employ the proportion of meso-lactide formed as an indicator. The proportion of meso-lactide formed is therefore desirably preferably 10 mol % or less of the lactide obtained, preferably 5 mol % or less, and more preferably 2 mol % or less.

In accordance with the present invention, lactide can be recovered while suppressing racemization, and the optical purity of the lactide obtained depends on the optical purity of the polylactic acid or derivative thereof used. That is, the higher the optical purity of the polylactic acid or derivative thereof used, the higher the optical purity of the lactide obtained. Therefore, when the optical purity of the polylactic acid or derivative thereof is 80% ee or higher, preferably 90% ee or higher, and more preferably 95% ee or higher, the optical purity of the lactide obtained by the chemical recycling increases proportionally. The '% ee' referred to here denotes enantiometric excess, expressed as the percentage excess of one of the enantiomorphs present in a mixture formed from the enantiomorphs.

In accordance with the present invention, since lactide having high optical purity is recovered efficiently from a polylactic acid, a derivative thereof, or a resin composition comprising same by a simple method, it has great potential as a chemical recycling method.

EXAMPLES

The present invention is explained below by reference to Examples, but the present invention is not limited to these Examples.

(Examples 1 to 6) and (Comparative Examples 1 to 4)

200 mg of poly(L-lactic acid) (PLLA) subjected to a hydrochloric acid treatment so as to contain hardly any metal (Mn=279000, Mw/Mn=1.90, tin content=17 ppm) and aluminum hydroxide, or alumina for Comparative Examples in an amount shown in Table 1 were placed in a sample tube, 5 mL of chloroform was added thereto, and intensive magnetic stirring was carried out at room temperature for 12 hours to give a PLLA solution in which aluminum hydroxide or alumina was uniformly dispersed. Subsequently, a cast film was formed from this solution in a flat petri dish. The surface of the cast film thus obtained was washed with methanol, and vacuum drying was carried out at room temperature for 1 day. Samples of about 5 mg at a time were cut out from the film thus obtained and subjected to thermal decomposition using a TG/DTA6200 manufactured by Seiko Instruments Inc. under an atmosphere of nitrogen at a rate of temperature increase of 5° C./minute in a temperature range from room temperature to 400° C. The results are shown in FIG. 1 and Table 1.

In the case of purified PLLA on its own, which did not contain aluminum hydroxide, (Comparative Example 1), the weight reduction due to decomposition started beyond 300° C. and the decomposition was almost complete at about 370° C. In contrast, the composition containing 10 parts by weight of aluminum hydroxide (Example 1) started thermally decomposing at around 250° C., and decomposition was almost complete at about 350° C. with 7.5 wt % residue remaining. The thermal decomposition temperature decreased in response to an increase in the aluminum hydroxide content, but in the case of 30 parts by weight or greater of aluminum hydroxide (Examples 3 to 6) there was hardly any change in the temperature of thermal decomposition, which started at around 250° C. and was complete at around 340° C. The thermal decomposition residue increased in proportion to the aluminum hydroxide content (Table 1). When aluminum hydroxide on its own was subjected to TG/DTA measurement under the same conditions, weight reduction due to thermal decomposition started at around 210° C. and proceeded rapidly until there was a residue of about 73 wt % at around 270° C. Subsequently, the weight reduction proceeded gradually and reached 65.9 wt % at 600° C., which is almost the same as the theoretical residual weight of 65.4 wt %. While taking into consideration this thermal decomposition behavior of aluminum hydroxide on its own, the decomposition residue of the compositions of Table 1 was compared with a weight reduction to about 73 wt % as an indicator and it was found that the values were very close to each other.

When thermal decomposition was carried out in the same manner as above using alumina instead of aluminum hydroxide, even if 10 to 30 parts by weight of alumina was added to 100 parts by weight of PLLA, the thermal decomposition temperature did not change at all, and the residue after thermal decomposition only increased in proportion to the amount of alumina added (Comparative Examples 2 to 4 in Table 1). From the results of these Examples and the Comparative Example, it has been found that the PLLA/aluminum hydroxide composition decreases the thermal decomposition temperature of pure PLLA by about 50° C., PLLA almost completely decomposes and vaporizes, and aluminum hydroxide changes into alumina, which is stable.

TABLE 1

| | PLLA/Al(OH)$_3$ PLLA/Al$_2$O$_3$ | | | Theoretical amount of residue |
|---|---|---|---|---|
| | Ratio by weight | Al compound (wt %) | Final residue (wt %) | (wt %) Al(OH)$_3$ → Al$_2$O$_3$ Conversion factor 73% |
| Comp. Ex. 1 | 100/0 | 0 | ≈0 | 0 |
| | PLLA/Al(OH)$_3$ | | | |
| Ex. 1 | 100/10 | 9.1 | 7.5 | 6.6 |
| Ex. 2 | 100/20 | 16.7 | 12.3 | 12.2 |
| Ex. 3 | 100/30 | 23.1 | 17.8 | 16.8 |
| Ex. 4 | 100/40 | 28.6 | 20.7 | 20.9 |
| Ex. 5 | 100/50 | 33.3 | 24.6 | 24.3 |
| Ex. 6 | 100/60 | 37.5 | 27.1 | 27.4 |
| | PLLA/Al$_2$O$_3$ | | | |
| Comp. Ex. 2 | 100/10 | 9.1 | 9.7 | |
| Comp. Ex. 3 | 100/20 | 16.7 | 16.3 | |
| Comp. Ex. 4 | 100/30 | 23.1 | 22.6 | |

(Example 7) and (Comparative Examples 5 to 6)

Pyrolysis gas chromatography mass spectrometry (Py-GC/MS) analysis was carried out using a film of the purified PLLA/aluminum hydroxide (100/30 ratio by weight) formed in Example 3. 10 µg of a film sample was rapidly charged into a pyrolysis oven preheated to 60° C. while passing an inert gas (helium) through a pyrolyzer equipped with a sampler (PY2020D manufactured by Frontier Laboratories Ltd., GC-17A +GCMS-QP5050 manufactured by Shimadzu Corporation). Subsequently, the temperature was increased up to 300° C. at 10° C./minute. Thermal decomposition products in a temperature range of 60° C. to 300° C. were sampled using the sampler, and analyzed using the GC/MS. From the results of the analysis, the proportion of lactide was 99.52% of the entire products, and the meso-lactide content was 0.56%. As products other than lactide, only 0.28% and 0.20% peaks were observed at positions that almost corresponded to the retention times of cyclic tetramer and pentamer respectively.

On the other hand, as Comparative Example 5, a similar sample was heated up to 400° C. at 10° C./minute. Thermal decomposition products in a temperature range of 60° C. to 400° C. were sampled using the sampler, and analyzed using the GC/MS. From the results of the analysis, the proportion of lactide was 96.64% of the entire products, and the meso-lactide content was 12.17%. As products other than lactide, cyclic trimer to hexamer were observed at 0.50%, 1.65%, 0.75%, and 0.46% respectively.

Furthermore, as Comparative Example 6, a film of the purified PLLA/alumina (100/30 ratio by weight) formed in Comparative Example 4 was heated up to 400° C. at 10° C./minute. Thermal decomposition products in a temperature range of 60° C. to 400° C. were sampled using the sampler, and analyzed using the GC/MS. From the results of the analysis, the proportion of lactide was 78.74% of the entire products, and the meso-lactide content was 18.28%. As products other than lactide, cyclic trimer to heptamer were observed at 3.26%, 5.59%, 6.02%, 4.51%, and 1.88% respectively.

From the results above, it is clear that lactide is selectively formed by aluminum hydroxide, and lactide formed at up to 300° C. has high optical purity.

(Example 8 to 12) and (Comparative Examples 7 to 8)

Pyrolysis gas chromatography mass spectrometry (Py-GC/MS) analysis was carried out using a film of the purified PLLA/aluminum hydroxide (100/30 ratio by weight) formed in Example 3. 10 μg of a film sample was rapidly charged into a pyrolysis oven preheated to 60° C. while passing an inert gas (helium) through a pyrolyzer equipped with a sampler (PY2020D manufactured by Frontier Laboratories Ltd., GC-17A+GCMS-QP5050 manufactured by Shimadzu Corporation). Subsequently, the temperature was increased up to a temperature shown in Table 2 at 10° C./minute. Thermal decomposition products in a predetermined temperature range were sampled using the sampler, and analyzed using the GC/MS. The analytical results are given in Table 2. From the results, formation of meso-lactide and cyclic oligomers was not observed at all in the temperature range 60-300° C. (Examples 8 to 11), and it was confirmed that almost pure L,L-lactide was obtained. In the range 60-320° C. (Example 12), formation of small amounts of meso-lactide and cyclic oligomers was observed at 6.08% and 2.00% respectively. Furthermore, in a high temperature region, formation of meso-lactide and cyclic oligomers was promoted (Comparative Examples 7 to 8).

From the above results, it has been found that, in order to convert the lactide obtained into a useful lactic acid polymer, it is necessary to maintain the optical purity of the recovered lactide at 80% ee or higher, and it is therefore preferable to set the thermal decomposition temperature region for PLLA at no greater than 320° C.

TABLE 2

| | Thermal decomposition temperature range (° C.) | Composition of decomposition product (%) | | |
|---|---|---|---|---|
| | | meso-Lactide | L,L-/D,D-Lactide | Oligomer |
| Ex. 8 | 60-270 | 0 | 100 | 0 |
| Ex. 9 | 60-280 | 0 | 100 | 0 |
| Ex. 10 | 60-290 | 0 | 100 | 0 |
| Ex. 11 | 60-300 | 0 | 100 | 0 |
| Ex. 12 | 60-320 | 6.08 | 91.92 | 2.00 |
| Comp. Ex. 7 | 60-340 | 7.54 | 89.00 | 3.46 |
| Comp. Ex. 8 | 60-400 | 12.17 | 84.47 | 3.36 |

(Example 13)

150 mg of a film of the purified PLLA/aluminum hydroxide (100/30 ratio by weight) formed in Example 3 was charged into a GTO-350D pyrolysis glass tube oven manufactured by Shibata Scientific Technology Ltd., and vacuum/nitrogen gas replacement was carried out three times. Subsequently, the temperature of the glass tube oven was gradually increased up to 280° C. under an atmosphere of nitrogen, and then maintained at that temperature for 2 hours. Thermal decomposition products recovered in a room temperature trap were analyzed using a GC-9A gas chromatograph manufactured by Shimadzu Corporation, which was equipped with a Varian cyclodextrine-β-236M-19 optical resolution capillary column (0.25 mm×50 m). From the results, the composition of the product was 95.30% of L,L-lactide, 4.19% of meso-lactide, and 0.51% of D,D-lactide.

(Examples 14 to 16) and (Comparative Example 9)

Figure 2:
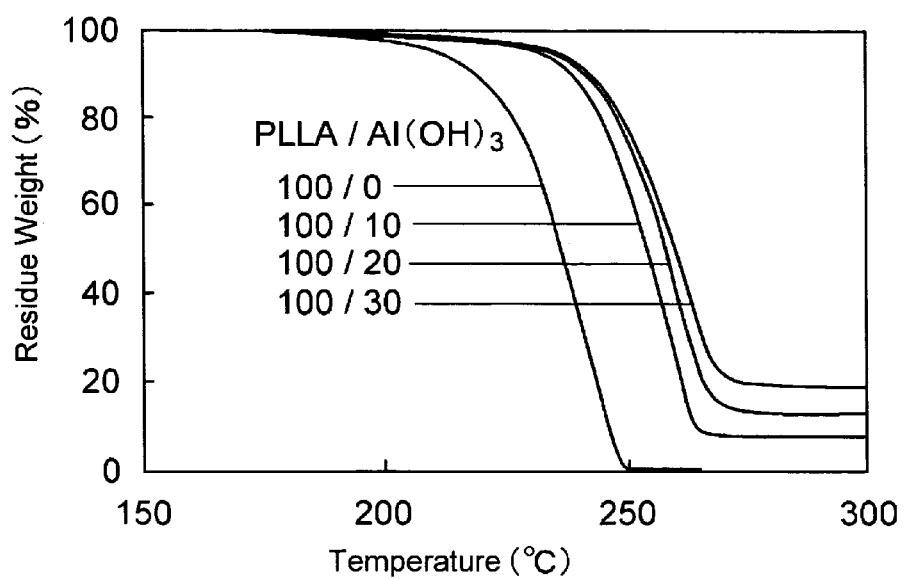

A sample tube was charged with 200 mg of PLLA (Mn=150000, Mw/Mn=2.48, tin content=388 ppm) synthesized using tin octanoate as a catalyst, and aluminum hydroxide in an amount shown in Table 3, 5 mL of chloroform was added thereto, and intensive magnetic stirring was carried out at room temperature for 12 hours to give a PLLA solution in which aluminum hydroxide was uniformly dispersed. Subsequently, a cast film was formed from this solution in a flat petri dish. The surface of the cast film thus obtained was washed with methanol, and vacuum drying was carried out at room temperature for 1 day. Samples of about 5 mg at a time were cut out from the film thus obtained and subjected to thermal decomposition using a TG/DTA6200 manufactured by Seiko Instruments Inc. under an atmosphere of nitrogen at a rate of temperature increase of 1° C./minute in a temperature range from room temperature to 400° C. The results are shown in FIG. 2 and Table 3.

In the case of tin-containing PLLA on its own, which did not contain aluminum hydroxide, (Comparative Example 9), weight reduction due to decomposition of PLLA started beyond 180° C. and the decomposition was almost complete at about 250° C. In contrast thereto, compositions containing 10 to 30 parts by weight of aluminum hydroxide (Examples 14 to 16) started thermally decomposing at around 200° C., and decomposition was almost complete at about 270° C. with an amount of residue remaining corresponding to the amount of aluminum hydroxide added. The conversion of aluminum hydroxide into alumina in this temperature range was 32-59%. From the results of these Examples and the Comparative Example, it is clear that the tin-containing PLLA/aluminum hydroxide composition gives an increase in the thermal decomposition temperature of about 20° C. compared with the tin-containing PLLA alone, the PLLA is almost completely decomposed and vaporized, and aluminum hydroxide partly changes into alumina, which is stable.

TABLE 3

| | PLLA/Al(OH)₃ | | Final | |
|---|---|---|---|---|
| | Ratio by weight | Al(OH)₃ (wt %) | residue (wt %) | Al(OH)₃ → Al₂O₃ Conversion factor (%) |
| Comp. Ex. 9 | 100/0 | 0 | ≈0 | |
| Ex. 14 | 100/10 | 9.1 | 8.1 | 32 |
| Ex. 15 | 100/20 | 16.7 | 13.3 | 59 |
| Ex. 16 | 100/30 | 23.1 | 19.0 | 51 |

(Examples 17 to 19)

A sample tube was charged with 100 mg of PLLA (Mn=150000, Mw/Mn=2.48, tin content=388 ppm) synthesized using tin octanoate as a catalyst, 100 mg of polystyrene (PSt) (manufactured by Scientific Polymer Products, Inc., Mw=280000), and aluminum hydroxide in an amount shown in Table 4, 5 mL of chloroform was added thereto, and intensive magnetic stirring was carried out at room temperature for 12 hours to give a PLLA/PSt solution in which aluminum hydroxide was uniformly dispersed. Subsequently, a cast film was formed from this solution in a flat petri dish. The surface of the cast film thus obtained was washed with methanol, and vacuum drying was carried out at room temperature for 1 day.

Figure 3:
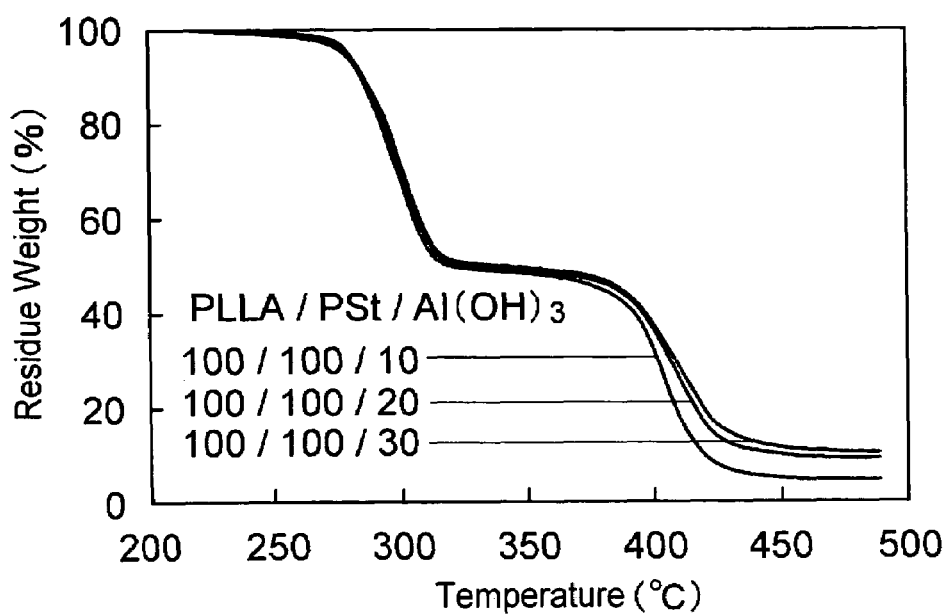

Samples of about 5 mg at a time were cut out from the film thus obtained and subjected to thermal decomposition using a TG/DTA6200 manufactured by Seiko Instruments Inc. under an atmosphere of nitrogen at a rate of temperature increase of 9° C./minute in a temperature range from room temperature to 500° C. The results are shown in FIG. 3.

The composition containing aluminum hydroxide started thermally decomposing at around 250° C., and first stage decomposition was complete at around 310° C., with about 50 wt % residue remaining. Second stage decomposition started at around 370° C. and was complete at around 450° C. with an amount of residue remaining corresponding to the aluminum hydroxide content. The results are shown in Table 4.

Pyrolysis gas chromatography mass spectrometry (Py-GC/MS) analysis was carried out using a film of the purified PLLA/PSt/aluminum hydroxide (100/100/30 ratio by weight) formed in Example 19. 10 μg of a film sample was rapidly charged into a pyrolysis oven preheated at 60° C. while passing an inert gas (helium) through a pyrolyzer equipped with a sampler (PY2020D manufactured by Frontier Laboratories Ltd., GC-17A+GCMS-QP5050 manufactured by Shimadzu Corporation). Subsequently, the temperature was increased up to 300° C. at 10° C./minute. Thermal decomposition products in a temperature range of 60° C. to 300° C. were sampled using the sampler, and analyzed using the GC/MS. From the results of the analysis, the proportion of lactide was 100% of the entire products, and the presence of meso-lactide or cyclic oligomers was not detected. These results show that, even when the polylactic acid/aluminum hydroxide composition contains polystyrene, which is a generally employed resin, polylactic acid decomposes at a temperature of 300° C. or less and is converted into lactide having high optical purity.

TABLE 4

| | PLLA/PSt/Al(OH)$_3$ | | |
| --- | --- | --- | --- |
| | Ratio by weight | Al(OH)$_3$ (wt %) | Final residue (wt %) |
| Ex. 17 | 100/100/10 | 4.8 | 4.2 |
| Ex. 18 | 100/100/20 | 9.1 | 8.6 |
| Ex. 19 | 100/100/30 | 13.0 | 10.5 |

INDUSTRIAL APPLICABILITY

In accordance with the present invention, it becomes possible to efficiently and easily produce and recover lactide having high optical purity from a polylactic acid or derivative thereof or a resin composition comprising same, and this is extremely effective for chemical recycling of used flame-retardant moldings formed from a polylactic acid or derivative thereof or a resin composition comprising same.

What is claimed is:

1. A method for recovering lactide from a polylactic acid or derivative thereof having an L- or D-lactic acid ester structural unit at 90% or greater of the entire units, the method comprising recovering lactide by thermally decomposing a mixture of a polylactic acid or derivative thereof and aluminum hydroxide at a temperature in a range from at least the melting temperature of the polylactic acid or derivative thereof to no greater than 320° C.

2. The method for recovering lactide from a polylactic acid or derivative thereof according to claim 1, wherein the mixture comprises a resin composition comprising the polylactic acid or derivative thereof and aluminum hydroxide.

3. The method for recovering lactide from a polylactic acid or derivative thereof according to claim 1, wherein the mixture comprises 10 to 100 parts by weight of aluminum hydroxide relative to 100 parts by weight of the polylactic acid or derivative thereof.

4. The method for recovering lactide from a polylactic acid or derivative thereof according to claim 1, wherein the polylactic acid or derivative thereof comprises a tin compound.

5. The method for recovering lactide from a polylactic acid or derivative thereof according to claim 1, wherein the thermal decomposition temperature is in a temperature range of 200° C. to 300° C.

6. The method for recovering lactide from a polylactic acid or derivative thereof according to claim 1, wherein the polylactic acid or derivative thereof has an optical purity of at least 80% ee, and the lactide obtained has a meso-lactide content of 10 mol % or less.

7. The method for recovering lactide from a polylactic acid or derivative thereof according to claim 1, wherein the derivative of the polylactic acid includes at least one unit derived from a copolymer component selected from the group consisting of a lactone, a cyclic ether, a cyclic amide, and a cyclic acid anhydride, which are copolymerizable with lactide, at 10% or less of the entire units, as the units other than lactic acid ester structural units.

8. The method for recovering lactide from a polylactic acid or derivative thereof according to claim 7, wherein the lactone is at least one selected from the group consisting of caprolactone, valerolactone, β-butyrolactone, and p-dioxanone.

9. The method for recovering lactide from a polylactic acid or derivative thereof according to claim 7, wherein the cyclic ether is at least one selected from the group consisting of ethylene oxide, propylene oxide, butylene oxide, styrene oxide, phenylglycidyl ether, oxetane, and tetrahydrofuran.

10. The method for recovering lactide from a polylactic acid or derivative thereof according to claim 7, wherein the cyclic amide is ε-caprolactam.

11. The method for recovering lactide from a polylactic acid or derivative thereof according to claim 7, wherein the cyclic acid anhydride is at least one selected from the group consisting of succinic anhydride and adipic anhydride.

12. The method for recovering lactide from a polylactic acid or derivative thereof according to claim 7, wherein the derivative of the polylactic acid is a copolymer of polylactic acid and a lactone.

13. The method for recovering lactide from a polylactic acid or derivative thereof according to claim 7, wherein the derivative of the polylactic acid is a copolymer of polylactic acid and a cyclic ether.

14. The method for recovering lactide from a polylactic acid or derivative thereof according to claim 7, wherein the derivative of the polylactic acid is a copolymer of polylactic acid and a cyclic amide.

15. The method for recovering lactide from a polylactic acid or derivative thereof according to claim 7, wherein the derivative of the polylactic acid is a copolymer of polylactic acid and a cyclic acid anhydride.

16. A method for recovering lactide from a polylactic acid, the method comprising recovering lactide by thermally decomposing a mixture of a polylactic acid and aluminum hydroxide at a temperature in a range from at least the melting temperature of the polylactic acid to no greater than 320° C.

17. The method for recovering lactide from a polylactic acid according to claim 16, wherein the polylactic acid is poly(L-lactic acid).

* * * * *